United States Patent [19]

Anzai et al.

[11] Patent Number: 4,846,159
[45] Date of Patent: Jul. 11, 1989

[54] MASSAGE APPARATUS

[75] Inventors: Masatsugu Anzai, Fukuoka; Takeo Imoto, Settsu, both of Japan

[73] Assignee: Kabushiki Kaisha Nihon Kenko Zoshin Kenkyukai, Fukuoka, Japan

[21] Appl. No.: 113,846

[22] Filed: Oct. 29, 1987

Related U.S. Application Data

[63] Continuation-in-part of Ser. No. 74,596, Jul. 17, 1987, abandoned.

[30] Foreign Application Priority Data

Aug. 22, 1986 [JP] Japan ............ 61-128604[U]
Jun. 12, 1987 [JP] Japan ............ 62-90982[U]

[51] Int. Cl.$^4$ ............................................. A61H 15/00
[52] U.S. Cl. ............................................. 128/57; 128/44; 128/62 R
[58] Field of Search ............ 128/57, 44, 56, 62 R, 128/67, 24.3, 41, 1.3, 1.4

[56] References Cited

U.S. PATENT DOCUMENTS

| 744,718 | 11/1903 | Cassidy | 128/57 |
| 1,239,539 | 12/1916 | Swenson | 128/57 |
| 2,258,931 | 10/1941 | Heer et al. | 128/57 |
| 2,447,269 | 8/1948 | Myers | 128/57 |
| 4,161,943 | 7/1979 | Nogier | 128/1.3 |
| 4,303,062 | 12/1981 | Vars | 128/1.3 |
| 4,391,270 | 7/1983 | Uragumi | 128/1.3 |

FOREIGN PATENT DOCUMENTS

| 0199872 | 5/1986 | European Pat. Off. | 128/1.3 |
| 2261566 | 8/1973 | Fed. Rep. of Germany . | |
| 2510173 | 9/1976 | Fed. Rep. of Germany | 128/1.3 |
| 3324119 | 1/1985 | Fed. Rep. of Germany | 128/1.3 |
| 192738 | 10/1985 | Japan | 128/1.3 |
| 61-82631 | 5/1986 | Japan . | |
| 0835646 | 5/1960 | United Kingdom | 128/1.3 |

Primary Examiner—David A. Wiecking
Assistant Examiner—Huong Q. Pham
Attorney, Agent, or Firm—Armstrong, Nikaido, Marmelstein, Kubovcik & Murray

[57] ABSTRACT

A massage apparatus adapted to be utilized for various massage manner comprising at least two balls which are provided with a mutiple numbers of projections on the outer periphery thereof and a case for enclosing and retaining the balls in a rotatable state by rotatably supporting a pair of projections of the balls and in attachable/detachable manner.

11 Claims, 12 Drawing Sheets

FIG. 3
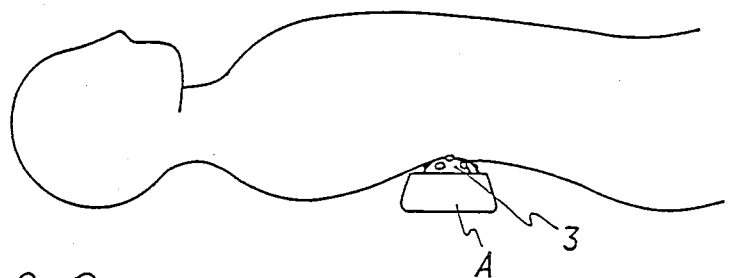
FIG. 2a
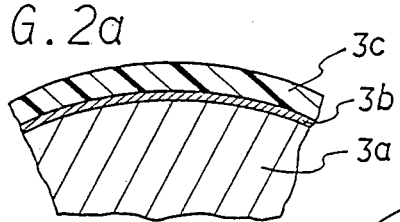
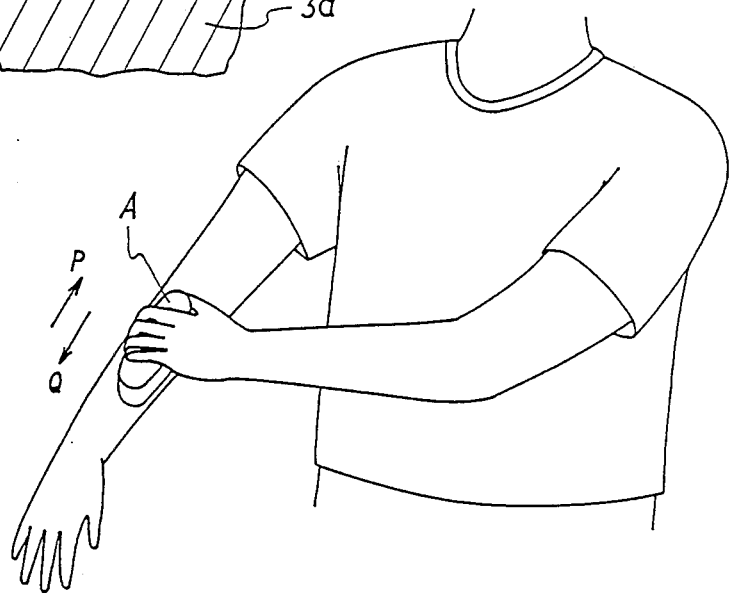
FIG. 4

MASSAGE APPARATUS

CROSS-REFERENCE TO RELATED APPLICATION

This is a continuation-in-part of application Ser. No. 074,596 filed on July 17, 1987, now abandoned.

BACKGROUND OF THE INVENTION

The present invention relates to a massage apparatus, and more particularly, to a massage apparatus which can be used for massaging a human body in various manners.

It is conveniently known that exercise of fingers by rolling two walnuts in the palm is effective for the rehabilitation of the patients with cerebrovascular disorder. A ball made of synthetic resin with a multiple number of projections on the surface (hereinafter referred to as "ball") is recently used as an alternative of such walnut. Such balls are usually placed in a case made of paper or the like for sale.

On the other hand, there has been known a wooden massage apparatus provided with two projections with approximately 65 mm pitch inbetween for giving pressure and stimulation to the two dorsal erectors in the human body. Such device, for example, is placed in the floor to press and stimulate the dorsal erectors of a person who lies on his back on the apparatus.

The prior art massage ball is used only to give stimulation to the palm, and the storing case is intended for the purpose of packaging alone.

An object of the present invention is to provide a massage apparatus which serves various purposes for massaging a human body by combining specifically structured balls and a case.

SUMMARY OF THE INVENTION

The massage apparatus of the present invention comprises at least two balls each of which is provided with a multiple number of projections on the outer periphery thereof and a rotary engaging member for supporting the ball in a rotatable state around an axis thereof, and a case for enclosing and retaining the balls. The case comprises a recessed portion for enclosing the balls in such manner that at least a part thereof protrudes outward and at least two pairs of supporting portions for supporting the rotary engaging members so as to allow rotary movement as well as attachment and detachment thereof.

It is preferable to provide projections of the ball as pairs each of which is arranged symmetrically with respect to the center of the ball. Such arrangement allows the use of an arbitrary pair of projections as the rotary engaging member.

In the apparatus of the present invention, the balls can freely rotate in such state that the balls are stored in the case. Therefore, by holding the massage apparatus in hand and by pressing the portion of the rotating balls protruding from the case against user's hand, leg, scruff of the neck, or abdomen, or to the body of another person, comfortable finger pressure effect can be obtained, since a multiple number of projections of the rotating balls give stimulation to the spots coming in contact with the projections one after another.

Further, when a ball or balls having magnetism are used, in addition to the general effect due to the magnetism, an advantage that blood circulation is effectively enhanced due to an alternating magnetic field can be obtained.

When the balls are taken out of the case, the balls can be used as ordinary massage balls for massaging the palm or for exercise of the fingers. Further, when the massage apparatus is placed on the floor with the balls enclosed in the case, and the user lies on his back on the apparatus, the two balls come in contact with the effective spots on the user's back to apply pressure corresponding to the user's weight.

Hereinafter, the massage apparatus of the present invention will be explained with reference to the accompanying drawings.

BRIEF DESCRIPTION OF THE DRAWINGS

FIG. 2a is a partial sectional view of the ball of FIG. 1;

FIG. 3 and FIG. 4 are illustrations showing respective used states of the massage apparatus A shown in FIGS. 1 and 2.

DETAILED DESCRIPTION OF THE INVENTION

Now referring to FIGS. 1 to 4, the first embodiment is described.

Figure 1:
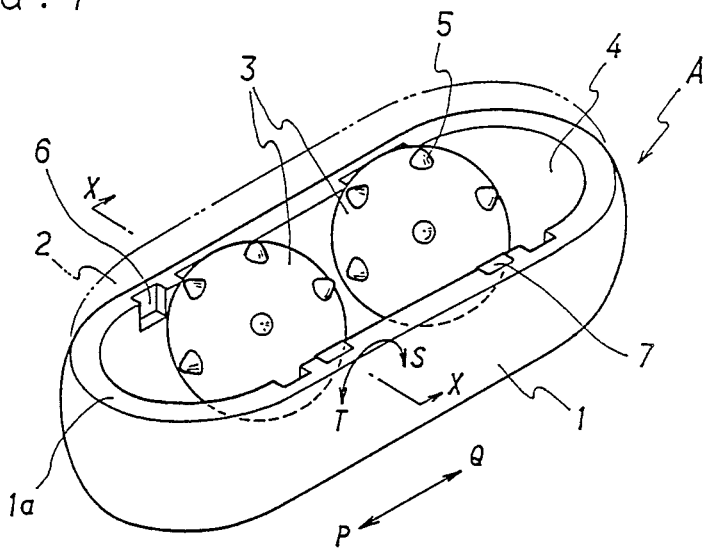
FIG. 1 is a perspective view showing a first embodiment of the massage apparatus of the present invention.
Figure 2:
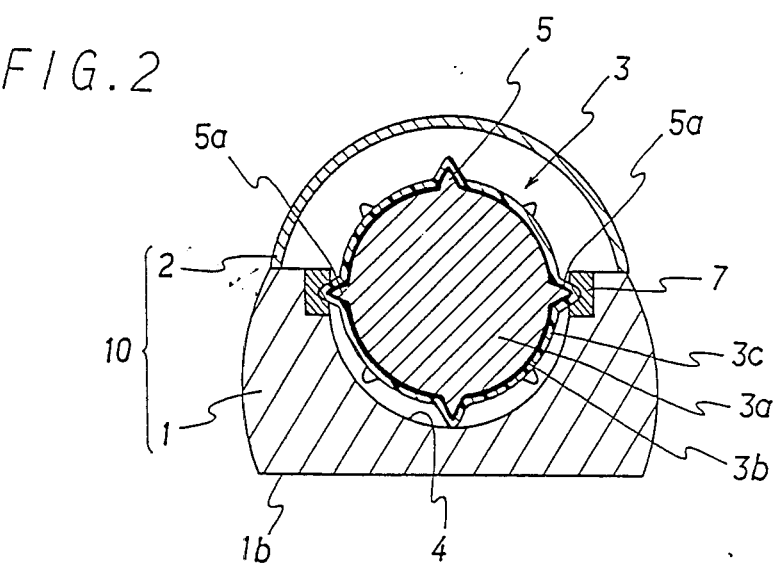
FIG. 2 is a cross sectional view along the line X—X of FIG. 1.

Referring to FIGS. 1 and 2, numeral 1 denotes a case which, together with a cover 2, constitutes a storing case 10. A recessed portion 4 is formed in the upper part of the case 1 for enclosing at least two balls 3. The recessed portion 4 is sufficiently large to hold, with remaining some margin, the two balls 3, for example, each having the diameter of approximately 28 mm with the pitch of 40–80 mm inbetween and deep enough to hold approximately a half portion of the ball.

Twelve conical projections 5 are provided on the outer periphery of the ball 3 with identical interval inbetween. In other words, each of those twelve projections is provided to protrude from the center of the respective face of an imaginary dodecagon circumscribed around the ball 3. Those projections are paired, each pair being symmetrical with respect to the center of the ball 3. An arbitrary pair of projections, therefore, can be used as a rotary engaging member. It is desirable to slightly round the tip of the projections so that damage or pain on the skin is advantageously prevented. Though the number and arrangement of the projections 5 are not limited to those described in the present embodiment, it is preferable to provide from eight to fifteen projections 5 in such a manner that at least a pair 5a are provided on the axis of the ball 3 to constitute rotary engaging member.

The upper face 1a of the case 1 is made flat and from three to five pairs of notched grooves 6 are formed at appropriate positions on the upper face 1a as bearing retainers. Rectangular parallelepiped bearing members 7 capable of rotatably supporting the projections 5a are fittably installed in an attachable/detachable manner to the notched grooves 6. Since the ball 3 is supported at its axis, approximately half the portion thereof protrudes from the upper face 1a. The bottom face 1b of the case 1 is made flat so that it can be placed on the floor or the like stably.

Though the number and the pitch of the notched grooves 6 are not specified in particular, generally from three to five pairs with the pitch of 10–15 mm are provided. The notched grooves 6 may be provided so as to extend in the longitudinal direction of the case 1 for continuously changing the pitch of the bearing members 7. In such case, appropriate fixture is provided to fix the position of the bearing members.

When the projections 5a which constitute rotary engaging member are provided separately from other projections 5, it is preferable to provide the former in a different form easily distinguishable, for example, in cylindrical shape, from that of the latter. The rotary engaging member may be structured in conically or similarly shaped recessed portion, and projections capable of rotatably engaging with the recessed portion may be provided in the bearing members 7.

The ball 3 used in the massage apparatus of the present invention may be approximately the same as the conventionally known massage ball. Rotary engaging member may be separately provided to such ball as required.

When it is intended to enhance blood circulation by providing magnetism to the ball 3, it is preferable, for example, to form the core part 3a of the ball 3 with the mixed material of polyamide resin or the like and ferrite. In that case, as shown in FIG. 2a, it is preferable to plate the outer surface of the core portion 3a with a gilt layer 3b, e.g. nickel gilt layer, and further to coat the outer surface of the gilt layer 3b with a synthetic resin layer 3c, e.g. polyamide resin layer. As described after, in case two balls 3 are rolled in the palm of user's hand, the outer surfaces of the balls 3 are rubbed with each other. Then, if only the gilt layer 3b is provided, there are disadvantages that metalic uncomfortable sound generates and the gilt layer 3b easily comes off. However, if the gilt layer 3b is coated with the synthetic resin layer 3c, the core portion 3a and the gilt layer 3b are advantageously protected by the resin layer 3c, and the user feels comfortable sound similar to that of walnuts when the balls 3 and/or the projections 5 come in contact with each other.

The case 1 may be formed with synthetic resin having good looking surface such as ABS or polyacetal resin, or other arbitrary material such as wood or metal.

It is preferable to form the bearing member 7 with a material having good sliding feature and abrasion resistance such as polyamide resin.

The cover 2 to be put on the case 1 may be formed with synthetic resin such as acryl resin, AS resin, GPPS resin or styrol resin. In order to enhance the display effect in a shopping store, the cover 2 is preferably made transparent. When two balls 3 having magnetism are set in the case 1 so that each pole axis is perpendicular with the rotational axis, rotation of one of the balls causes rotation of the other ball due to the magnetism, and the display effect is further enhanced.

The usage of the massage apparatus A having the structure shown in FIGS. 1 and 2 is now described hereinafter.

As shown in FIG. 3, when a massage apparatus A is placed on the floor with the balls 3 stored in the case 1, and a person lies on his back on the massage apparatus A, the two balls 3 come in contact with the effective spots on the back, and a finger pressure effect corresponding to the weight of the user is obtained. Since there is individual difference in the distance between the two dorsal erectors, the interval between the balls is adjusted by appropriately selecting the notched grooves 6 to hold the bearing members 7, and therefore, a desirable finger pressure effect along the dorsal erectors can be obtained, regardless of the physical constitution of the users.

As shown in FIG. 4, by holding the massage apparatus A in hand and moving it toward the direction of P-Q indicated by arrow to rotate the balls 3 while pressing them against the hand, leg, scruff of the neck, shoulder or abdomen of the user, or against another person's body, a multiple number of projections 5 of the rotating balls 3 come into contact with the skin and the effective spots and stimulate the same one by one, thereby achieving agreeable finger pressure effect. In that case, the balls are rotated to the direction of S-T indicated by arrow by the movement of the case 1 to the direction of P-Q indicated by arrow.

The balls 3, when taken out of the case and held in a palm of hand, may be used as ordinary massage balls for massaging the palm or exercise of the fingers.

Hereinafter, the second embodiment of the apparatus of the present invention is described with reference to FIGS. 5 to 9. In the second embodiment, rotational axes of the balls 3 are aligned along the longitudinal center axis of the case 1.

Figure 5:
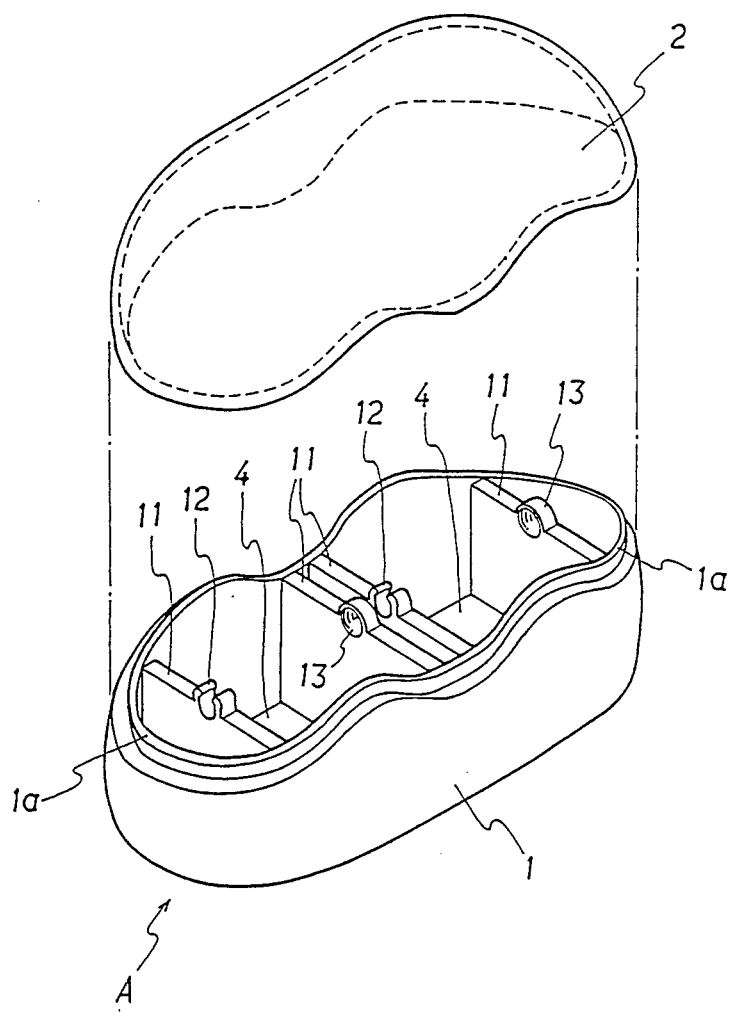
FIG. 5 is a perspective view showing a case and a cover of a second embodiment of the apparatus of the present invention.

As shown in FIG. 5, four walls 11 made of, for example, polyamide resin are securely inserted in the inner space of the case 1. Each space enclosed by a pair of walls 11 constitutes a recessed portion 4 for storing each ball 3. If the walls 11 are formed separately from the case 1, the case 1 is preferably made of polyacetal resin or the like having a good glossy surface. However, if the walls 11 are integratedly formed with the case 1, the whole may be made of a polyamide resin or the like. On the upper portions of the pair of walls 11, there are formed a set of supporting portions 12 and 13 aligning along the longitudinal axis of the case 1.

Figure 7:
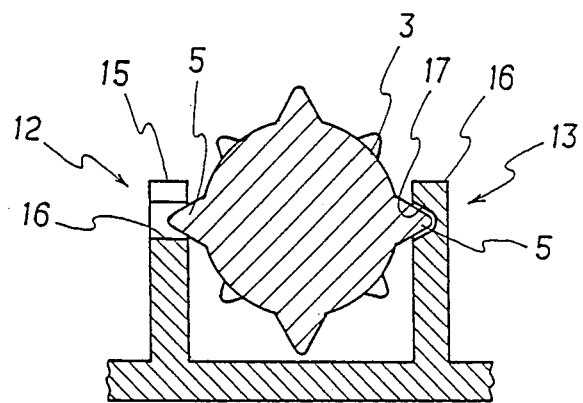
FIG. 7 is a cross sectional view showing the ball 3 in FIG. 6 in a supported state.
Figure 8:
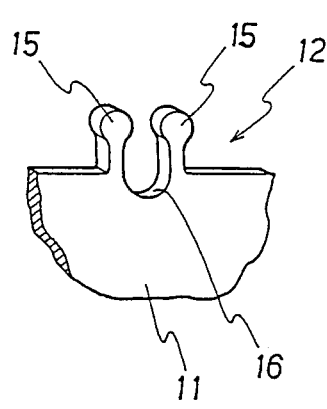
FIGS. 8 and 9 are perspective views showing the supporting portions in FIG. 6, respectively.
Figure 9:
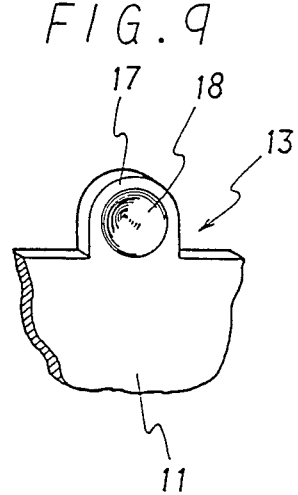

As shown in FIGS. 7 and 8, a supporting portion 12 comprises a pair of projecting pieces 15 arranged so as to make a gap or hole 16 which narrows at upper portion. Another supporting portion 13 is an inner surface of a conical hole 18 provided in a raised portion 17 as shown in FIGS. 7 and 9. The supporting portions 12 and 13 are provided as a set on the pair of walls 11 for supporting the ball 3, respectively. When the user intends to insert the ball 3 in the space, at first, a certain projection 5 is inserted in the hole-like supporting portion 13 and then the opposite side projection 5 is pressed into the gap between the two projecting pieces 15. Then the projecting pieces are elastically bent to receive the projection 5. After the projection 5 is inserted, the ball 3 is securely held by means of the supporting portions 12, 13 since the distance between the projecting pieces 15 at upper side thereof is narrowed.

In case one intends to detach the ball 3 from the supporting portions, by pulling up the ball 3 at the supporting portion 12 side, the ball 3 can be easily detached since the projecting pieces are elastically bent outwardly again.

Figure 6:
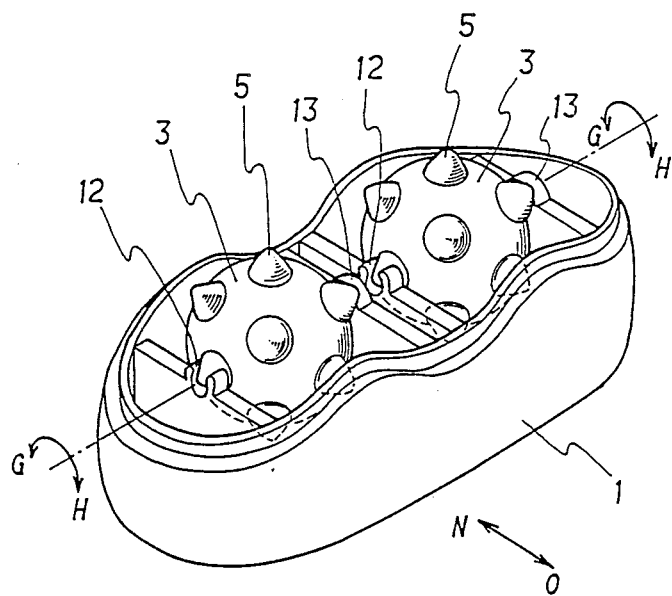
FIG. 6 is a perspective view showing the apparatus of the second embodiment of the present invention in a used state.

FIG. 6 shows a state where the balls 3 are set in the recessed portions 4. As shown in the drawings, in the present embodiment, the balls 3 rotate about the longitudinal axis of the case 1 in the direction of G-H indicated by arrow. Therefore, in the present embodiment, when the case 1 is moved in the lateral direction O-N indicated by arrow, massage effect is obtained.

In the present embodiment, both supporting portions can be made as a type having a pair of projecting pieces 15, i.e. a type of projecting portion 12 shown in FIG. 8. In that case, when the ball 3 is detached from the supporting portions, if keeping the posture of the ball horizontal and the ball 3 is pulled up straightly, the ball 3 cannot be easily detached since both pair of projecting pieces are bent at the same time. However, if one projection is pulled up in the slant direction at first and then the remain projection is pulled, the ball 3 can be easily detached since the projections are taken out one after another.

The present embodiment of the massage apparatus A can be used for massaging any part of user's body by rotating balls 3 thereon, as shown in FIG. 4. However, the massage apparatus can be comfortably used specially for massaging scruff of the user's neck or the shoulders since the case 1 is adapted to be moved in the lateral direction.

The upper surface 1a of the case 1 is formed in a wave-like shape. Further, both upper end portions of the upper surface 1a are made round. Therefore, the upper surface 1a smoothly touches user's body without rubbing with corners.

Figure 10:
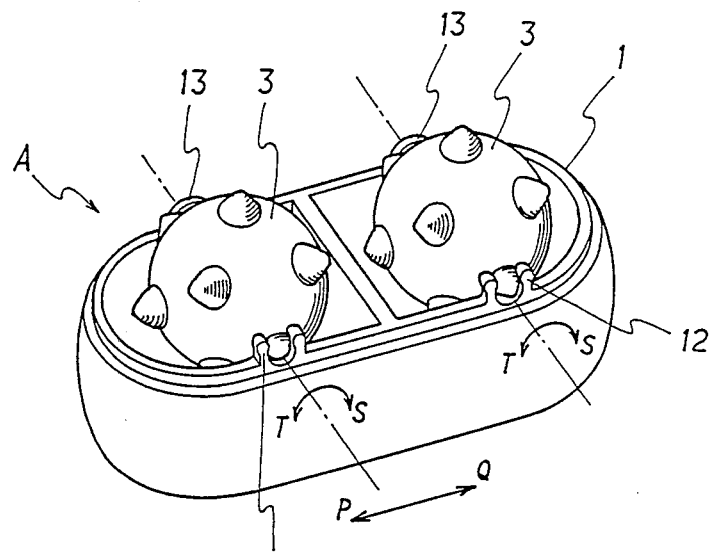
FIG. 10 is a perspective view showing a third embodiment of the present invention.

The third embodiment of the apparatus of the present invention shown in FIG. 10 is a compromise between the first embodiment and the second embodiment. In the apparatus A of FIG. 10 has a set of supporting portions 12 and 13 for supporting a ball 3. The supporting portions 12 and 13 are arranged in the lateral directions, and therefore, the balls 3 rotate in the direction of T-S denoted by arrows as same as the first embodiment.

In the present embodiment, also both supporting portions can be made as a type having a pair of projecting pieces 15 (see FIG. 8).

The massage apparatus of the present embodiment can be used in the same manner as described above with respect to the first embodiment.

Figure 11:
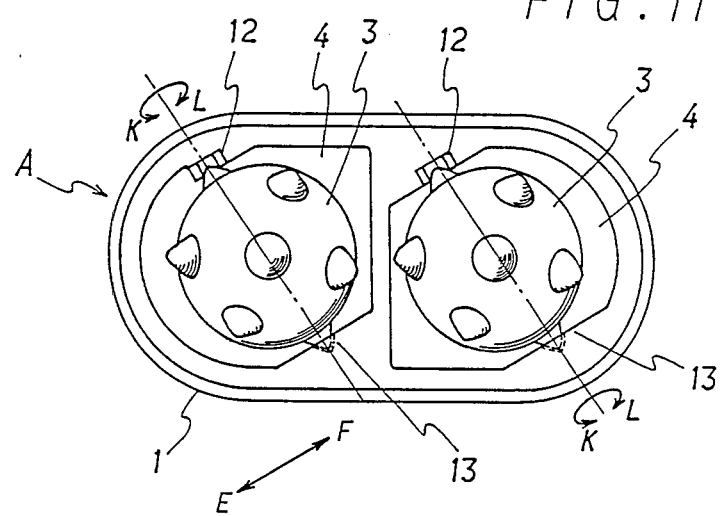
FIG. 11 is a plan view showing a fourth embodiment of the apparatus of the present invention.

FIG. 11 shows the fourth embodiment of the massage apparatus of the present invention.

In the apparatus of the present invention, the directions of rotational axes of the balls can be optionally selected. Therefore, the rotational axis can be arranged in an oblique direction unlike any embodiments mentioned above.

As shown in FIG. 11, the massage apparatus A of the present embodiment has supporting portions 12 and 13 which are crossing with the longitudinal axis of the case 1 in an oblique direction at the upper surface of the case 1. The remains are the same as the above-mentioned third embodiment.

In the present embodiment, when the case 1 is obliquely moved, i.e. in the direction of arrow E-F, the balls 3 roll in the direction of arrow K-L. The massage apparatus of the present embodiment can be used as same as the previously described any embodiments for massaging various parts of user's body.

Figure 12:
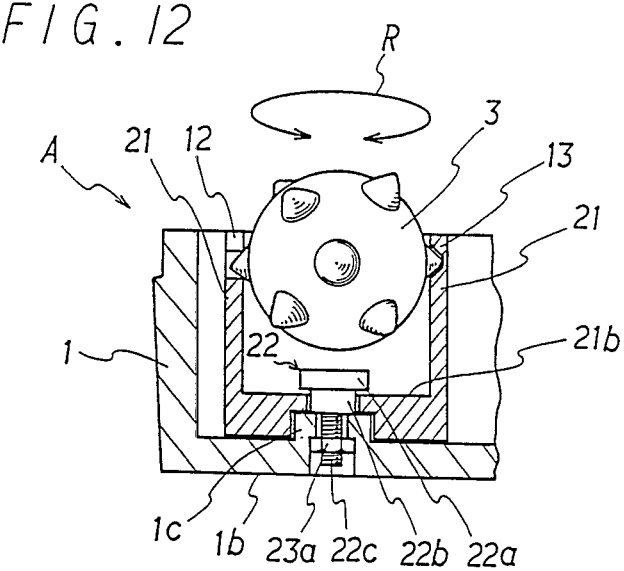
FIG. 12 is a sectional view showing a part of a fifth embodiment of the present invention.
Figure 13:
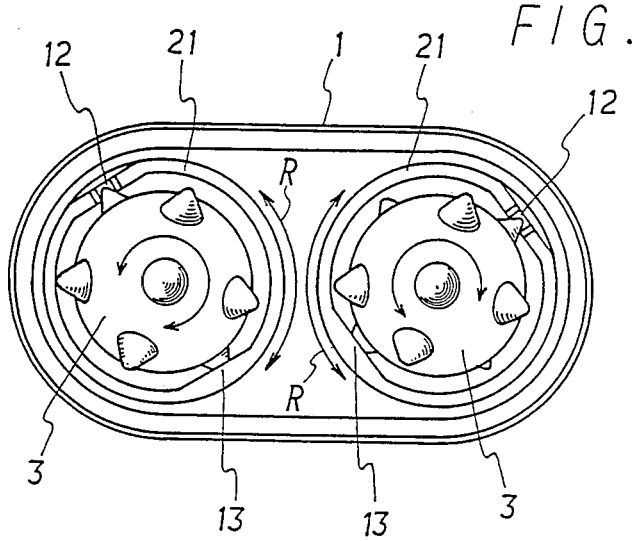
FIG. 13 is a plan view showing a sixth embodiment of the present invention.

The fifth embodiment relates to an apparatus shown in FIGS. 12 and 13. In this embodiment, a set of supporting portions 12 and 13 for receiving a ball 3 is freely rotatably about a vertical axis.

As shown in FIGS. 12 and 13, the supporting portions 12, 13 are formed on the upper end of a cylinder member 21. The cylinder member 21 is a short cylindrical body having its bottom end and can receive a lower half part of the ball 3. Though the set of supporting portions 12 and 13 in FIGS. 12 and 13 are the same as that of FIGS. 8 and 9, of course any type of supporting portions can be employed. For example, two supporting portions 12 of FIG. 8 can be employed.

The bottom portion 21b of the cylinder member 21 is mounted for allowing free rotation on a base portion 1b of the case 1 with a pin 22. The pin 22 comprises a head 22a, a stem 22b and a threaded portion 22c and is fixed on the case 1 with a nut 23a. The base portion 1b of the case 1 is provided with a raised portion 1c, and the bottom portion 21b of the cylinder member 21 is inserted between the raised portion 1c and the head 22a of the pin 22 with some clearance.

According to the above-mentioned structure, the cylinder member 21 can freely rotate in the direction of R about an axis of the pin 22. However, it is to be understood that the rotational mechanism in the present embodiment is not limited to the above-mentioned type, and any mechanism capable of realizing the function mentioned above can be employed. It is preferable that the cylinder member 21 and the pin 22 are made of polyamide resin or the like.

The apparatus of the present embodiment is suitable for massaging user's scruff of the neck or shoulders, since the direction of the rotational axis of the ball 3 can be freely changed.

Figure 14:
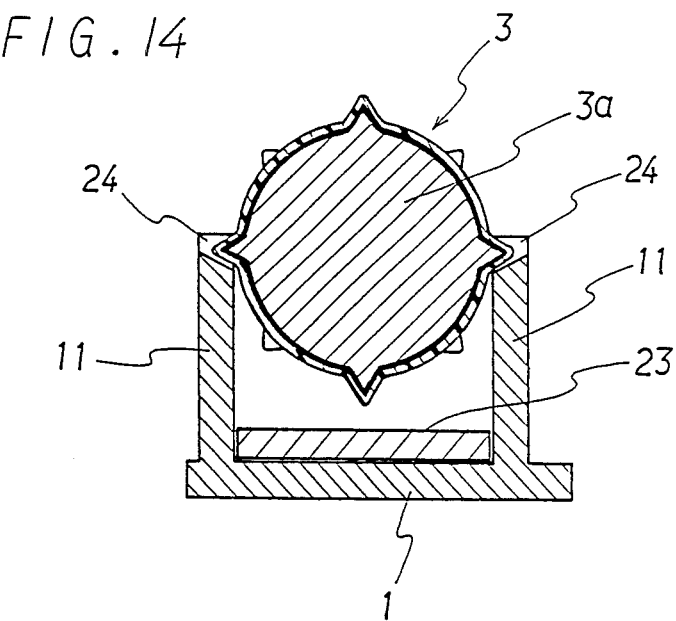
FIG. 14 is a partially sectional view of the sixth embodiment.

FIG. 14 shows the sixth embodiment in which magnetic force is utilized for holding the ball 3.

As shown in FIG. 14, a magnet plate or a magnetic substance 23 such as a steel plate is fixed in the base portion enclosed by the walls 11. In case a core portion 3a of the ball 3 has magnetism, the ball 3 does not freely come out of the case 1 sine the magnetic substance 23 and the ball 3 attract each other.

Figure 15:
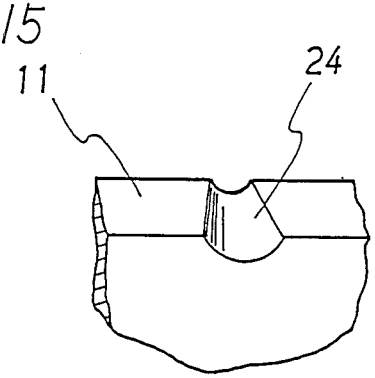
FIG. 15 is a perspective view showing the supporting portion 24 shown in FIG. 14.

In the present embodiment, it is not required to securely hold the ball 3 on the supporting portions. Therefore, a type of supporting portion 24 having a semiconical groove with only lower half part for example shown in FIG. 15 where upper side is completely opened, can be employed. When this type of supporting portion 24 with the semi-conical groove is employed, the ball 3 can be very easily attached to and detached from the supporting portions 24, and the apparatus can be conveniently used.

The advantageous construction of the present embodiment can be applied in any preceding embodiments.

Figure 16:
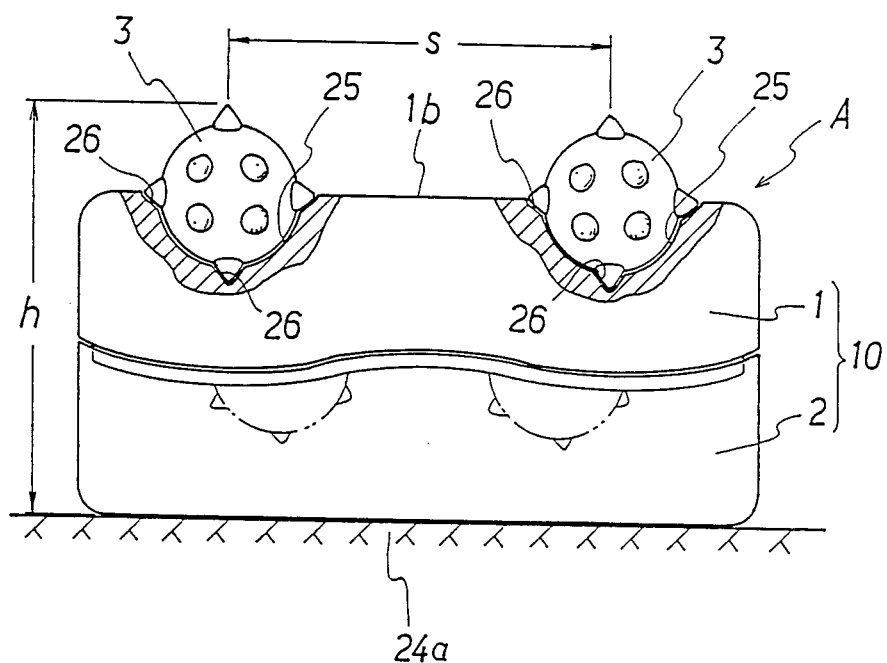
FIG. 16 is a front view showing a seventh embodiment in a state of use.

FIG. 16 shows the seventh embodiment which is suitable for massaging user's waist or back.

As shown in FIG. 16, a storing case 10 is put on a bed or floor 24a in a turned-over state. In the present embodiment, any one of mechanisms for rotatably supporting the ball 3 in the case 1 described in the preceding embodiments can be used. Characteristic feature of the present embodiment exists in an under surface of the case 1. In the under portion 1b of the case 1, two recessed portions 25 are formed. The recessed portion 25 has sufficient depth for containing about half of the ball 3, and has also a plural of small recesses 26 for receiving projections 5 of the ball 3. Therefore, after the ball 3 is inserted in the recessed portion 25, rotary movement of the ball 3 is restricted and the ball 3 cannot rotate.

Distance S between the two recessed portions 25, 25 is preferably about 65 mm in order to enable to easily push the user's dorsal erectors. Further, height h of the top surface of the ball 3 from the top surface of the cover 2, i.e. from the floor surface, is preferably about 65 mm.

The massage apparatus A of the present embodiment is used in an order described below.

The cover 2 is taken off from the case 1, the balls 3 (shown with imaginary lines in the drawings) are removed. Then the cover 2 is put on the case 1 again, and then they are turned upside down and are put on a bed or a floor 24a. Further, the previously removed balls 3 are inserted into the recessed portions 25, respectively. Then preparation for massage is completed.

Under the above situation, when the user lies on his back on the apparatus A, as shown in FIG. 3, the two balls 3 come in contact with effective spots of user's back and waist.

Though in the above-mentioned embodiments, only wo balls 3 are contained in the case 1, for example, four balls 3 may be contained in the case 1 so that the user can have two balls in his respective hand.

Hereinafter, functions and effects of the massage apparatus of the present invention in which balls having magnetism are employed are explained with reference to FIGS. 17 to 22.

Figure 17:
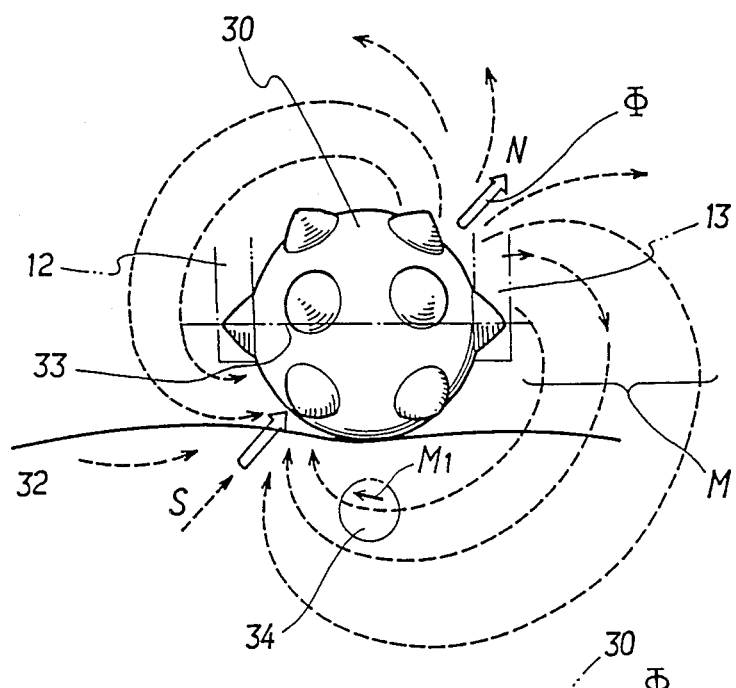
FIGS. 17 to 19 are illustrations showing functions of alternating field in the massage apparatus of the present invention.

Referring to FIG. 17, since lines of magnetic force M are passing from N-pole to S-pole of the ball 30 having magnetism, the lines of magnetic force M exert magnetic effect on blood vessels and nerveses passing the inside of the cutis or the skin 32 when the ball 30 is pressed on the surface of the skin 32. As a result, only by pressesing the ball 30 on the skin, "blood circulation enhancing effect" can be obtained in addition to the pressure stimulus due to projections 5.

In case that the projections 5 themselves are made of magnetic material, the lines of magnetic force M are concentrated to points of the projections 5, and therefore, the above-mentioned effect is further progressed. The magnetic field of the ball has an intensity of about 900 to 100 gausses for example. The inensity is not limited to the above exent.

As mentioned above, an extent of enhancing effect for blood circulation due to the magnetism can be obtained only by pressing the ball 30 on the skin. However, when the ball of the present invention is rotated on the skin in a contained state in a case or when only balls are rotated in a user's hand, a further excellent blood circulation enhancing effect due to the alternating magnetic field can be obtained as mentioned after.

In this specification, "alternating magnetic field" is a broad concept including not only the typical case in the electromagnetism where direction and magnitude of the lines of magnetic force periodically change like a sine-curve, but also a case where the direction and magnitude of the lines of magnetic force are repeatedly changed in an extent, a case where the polarity at the portion of the ball repeatedly becoming in contact with the skin irregularity changes, and the like.

At first, the ball 30 is supported by utilizing a pair of projections 5a and 5b as shown in FIG. 17, so that a straight line crossing the polar axis is selected as a rotational axis. In that case, if the polar axis is previously provided at the position avoiding the projections 5, the ball can be easily set on the case since the polar axis crosses with the rotational axis for any pair of projections.

Figure 18:
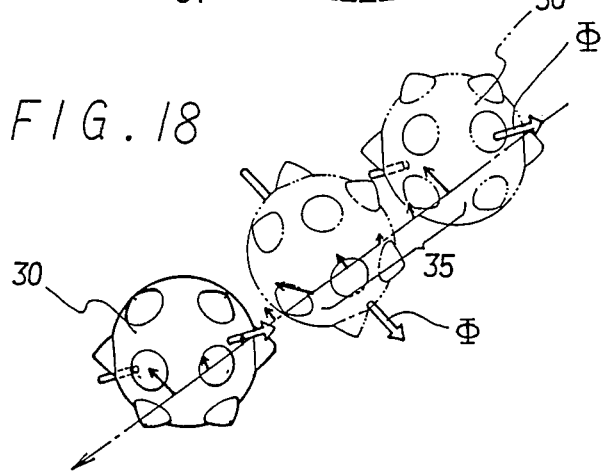
Figure 19:
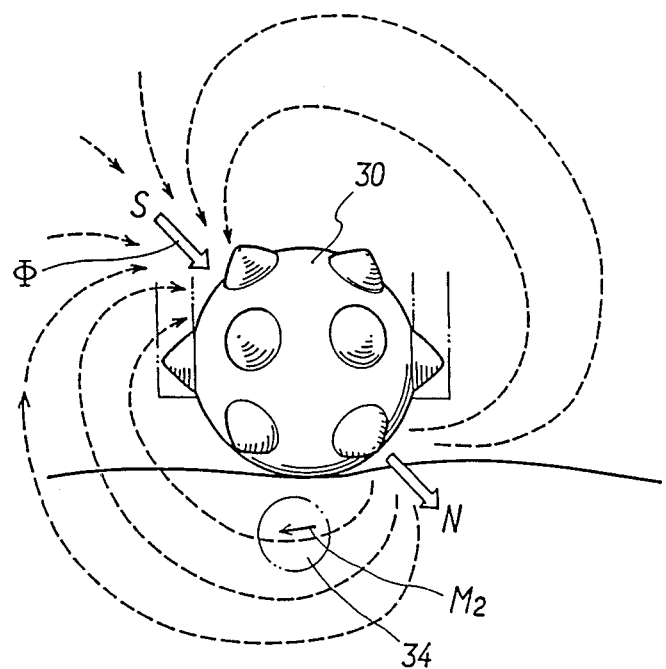

When the ball 30 set as mentioned above is rolled on the user's skin 32, the direction of polar axis Φ gradually changes in accordance with the roll of the ball 30 as shown in FIG. 18. Therefore, the direction and magnitude of the lines of magnetic force M gradually changes. For example, in the inner portion 34 of the skin being in contact with the ball 3, though the direction of the lines of magnetic force M is denoted by arrow M1 in FIG. 17, the direction of the lines changes to a direction denoted by arrows M2 in FIG. 19.

Accordingly, when a ball 30 straightly rolls over a skin 32, as shown with a series of arrows 35 of FIG. 18, the magnitude and direction of the lines of magnetic field change in an order, for example in an extent of about 90° in course of the roll, and therefore, alternating magnetic field is applied to the inner portion of the skin.

Such alternating magnetic field applies an electromagnetic force to charged particles, e.g. ions, flowing through the blood vessels, and the effect of enhancing the blood circulation is further progressed.

Figure 20:
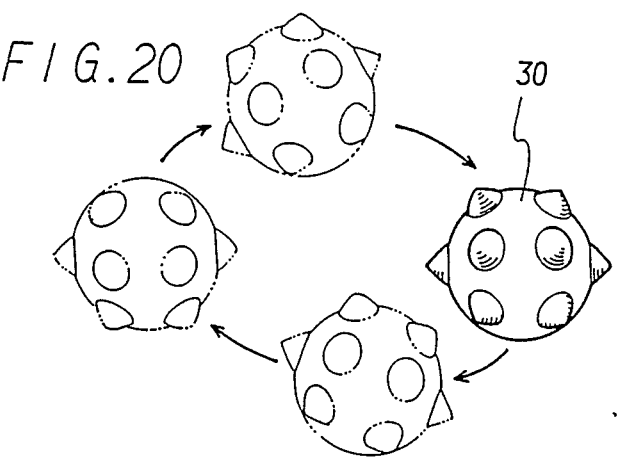
FIGS. 20 to 22 are illustrations showing methods for using the massage apparatus of the present invention.

As a method for rolling balls over the skin, various methods can be employed. That is to say, the ball can be rolled along a straight line as shown in FIG. 18, and further, for example, the ball 30 can be rolled so as to draw a circle or an oval as shown in FIG. 20. In the latter case, the effect of alternating magnetic field can be concentrated within a narrow limit since a series of lines of magnetic force alternating the direction thereof is applied on the same position of the skin.

Figure 21:
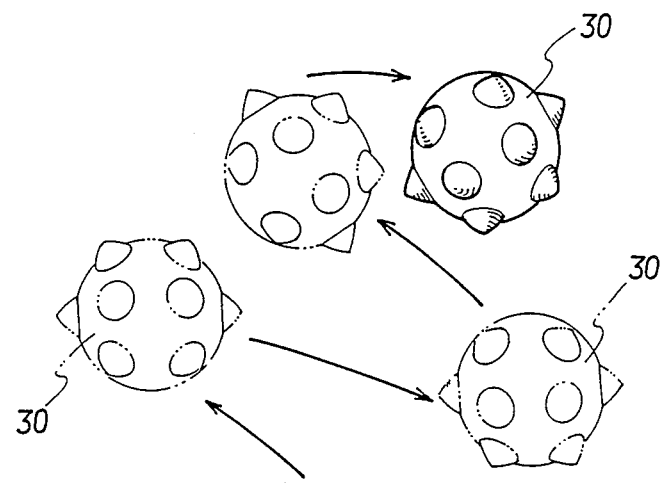

In addition, the ball 30 may be repeatedly pressed and slightly rolled over the skin so that the ball 30 rotates in the same direction, the pressing area may be shifted while drawing a circle or oval, and further the ball may be rolled along a zig-zag line as shown in FIG. 21. The above-mentioned using manner can be sufficiently carried out with the massage apparatus, for example, shown in FIG. 6 or FIG. 11 having a constant rotational axis. However, the massage apparatus shown in FIGS. 12 and 13 having a rotational axis of which direction is freely changeable is most adapted to the above using manner.

Though the above-mentioned magnetic functions can be obtained when a ball is used or only one of the balls has magnetism, the additional function mentioned after can be obtained when two balls having magnetism are employed.

Figure 22:
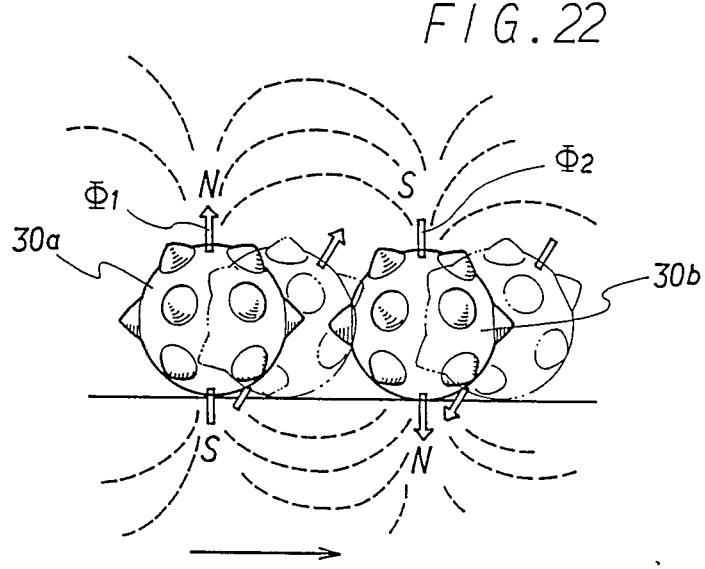

FIG. 22 shows a massage apparatus comprising a case and two balls 30 held in the case. In the present embodiment, the two balls 30a and 30b attract and repeal each other, and the polar axises Φ1 and Φ2 direct in the opposite directions.

Under the situation, when the pair of balls 30a and 30b are pushed against the skin, high-densed lines of magnetic force M pass from N-pole of one of the balls 30a to S-pole of the other ball 30b. Accordingly, even when the balls are pressed without rotation, a superior effect for enhancing blood circulation can be obtained.

Further, when the pair of balls 30a and 30b is rolled along the same straight line or along the same circle, alternation of the direction of the lines of magnetic force M becomes more rapid and great to further accelerate the effect of enhancing blood circulation.

Another advantage is that the relationship of the directions of the polar axes is usually held even if one of balls races, since the racing ball follows to the other driven ball.

If required, by changing the crossing angle between the rotational axis and the polar axis, or by adjusting or the distance between the balls as shown in the embodiment of the massage apparatus, the characteristics, e.g. magnitude and cycle, of the alternating magnetic field can be changed in accordance with the user's symptons of the stiffness of the shoulders to be cured.

The massage apparatus of the present invention can be used for massage in various manners, and the effect of massage is developed in comparison with conventional massage apparatus. Further, by using magnetized balls, an superior effect of enhancing blood circulation due to alternating magnetic field can be obtained.

Though several embodiments of the invention are described above in detail, it is to be understood that the present invention is not limited to the above embodiments, and various changes and modifications may be made in the invention without departing from the spirit and scope thereof.

What is claimed is:

1. A massage apparatus comprising:
at least two balls each of which is provided with a multiple number of projections on an outer periphery thereof and a rotary engaging member for supporting each of said balls in a rotatable state around an axis thereof; said projections of said balls being arranged as pairs symmetrical to the center of said ball and each ball has an arbitrary pair of said projections serving as said rotary engaging members and a case for enclosing and retaining said balls; wherein said case comprises a recessed portion to enclose said balls in such a manner that at least a part of each of said balls protrudes outward therefrom and at least two pairs of supporting portions for supporting said rotary engaging members of said balls so as to allow rotation and attachment/detachment thereof.

2. The massage apparatus of claim 1 wherein said supporting portions comprise bearing members for rotatably supporting said arbitrary pairs of said projections of said balls and bearing retainers for fittably receiving said bearing members in attachable/detachable manner.

3. The massage apparatus of claim 1 wherein said supporting portions are integratedly formed with said case and disposed on a longitudinal axis of said case.

4. The massage apparatus of claim 1 wherein said supporting portions are integratedly formed with said case and disposed on a line perpendicular to a longitudinal axis of said case.

5. The massage apparatus of claim 1 wherein said supporting portions are integratedly formed with said case and disposed on a line obliquely crossing with a longitudinal axis of said case.

6. The massage apparatus of claim 1 further comprising a cylinder member provided in said case mounted for rotating movement around a vertical axis and having an upper end, and wherein said supporting portions are formed on said upper end of said cylinder member.

7. The massage apparatus of claim 1 wherein said balls have magnetism.

8. The massage apparatus of claim 7 wherein each of said arbitrary pairs defines a rotational axis of said balls and a polar axis of each of said balls is disposed at an angle to said rotational axis of each of said balls.

9. The massage apparatus of claim 7 wherein a magnetic substance is fixed in said case, and said balls are held on said supporting portions by utilizing magnetic attracting force between said balls and said magnetic substance; said balls and said magnetic substance being spaced apart.

10. A massage apparatus comprising:
at least two balls each of which is provided with a multiple number of projections on an outer periphery thereof and a rotary engaging member for supporting each of said balls in a rotatable state around an axis thereof; at least two of said projections of each of said balls being arranged as a pair symmetrical to the center of said ball and serving as said rotary engaging members; a case for enclosing and retaining said balls; said case having a first recessed portion to enclose said balls in such a manner that at least a part of each of said balls protrudes outward therefrom and at least two pairs of supporting portions for supporting said rotary engaging members of said balls so as to allow rotation and attachment/detachment thereof; and said case having small recesses for receiving said projections of said balls so as not to allow rotation of said balls.

11. A massage ball comprising a core member made of synthesized resin and ferrite; said core member being provided with a multiple number of projections on an outer surface thereof; a protective layer provided on said core member, said protective layer comprising a metal layer and an outside layer comprising a synthesized resin layer.

* * * * *